(12) United States Patent
Hope

(10) Patent No.: US 6,447,800 B2
(45) Date of Patent: *Sep. 10, 2002

(54) METHOD OF LOADING PREFORMED LIPOSOMES USING ETHANOL

(75) Inventor: Michael J. Hope, Vancouver (CA)

(73) Assignee: The University of British Columbia (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/588,542

(22) Filed: Jan. 18, 1996

(51) Int. Cl.[7] ............................................. A61K 9/127
(52) U.S. Cl. .................... 424/450; 424/1.21; 424/9.321; 424/9.51; 424/417; 935/54; 264/4.1; 264/4.3; 264/4.6
(58) Field of Search ............................ 424/450, 1.21, 424/9.321, 9.51, 417, 94.3; 436/829; 935/54; 264/4.1, 4.3, 4.6

(56) References Cited

U.S. PATENT DOCUMENTS

| | | | |
|---|---|---|---|
| 4,224,179 A | 9/1980 | Schneider | 252/316 |
| 4,235,871 A | 11/1980 | Papahadjopoulos et al. | 424/19 |
| 4,389,330 A | 6/1983 | Tice et al. | 427/213.36 |
| 4,515,736 A | 5/1985 | Deamer | 264/4.3 |
| 4,683,092 A | 7/1987 | Tsang | 264/4.3 |
| 4,814,270 A | 3/1989 | Piran | 435/7 |
| 4,877,561 A | 10/1989 | Iga et al. | 264/4.3 |
| 4,946,683 A | 8/1990 | Forssen | 424/422 |
| 4,952,408 A | 8/1990 | Rahman | 424/450 |
| 4,994,213 A | 2/1991 | Aitcheson et al. | 264/4.6 |
| 5,049,392 A | 9/1991 | Weiner et al. | 424/450 |
| 5,077,056 A | 12/1991 | Bally et al. | 424/450 |
| 5,082,664 A * | 1/1992 | Leuk | 424/450 |
| 5,104,661 A | 4/1992 | Lau | 424/450 |
| 5,171,578 A | 12/1992 | Bally et al. | 424/450 |
| 5,192,549 A | 3/1993 | Barenolz et al. | 424/450 |
| 5,204,112 A | 4/1993 | Hope et al. | 124/450 |
| 5,262,168 A | 11/1993 | Lenk et al. | 424/450 |
| 5,284,588 A | 2/1994 | Makowski et al. | 210/638 |
| 5,316,771 A | 5/1994 | Barenholz et al. | 424/450 |
| 5,380,531 A | 1/1995 | Chakrabarti et al. | 424/450 |
| 5,393,530 A | 2/1995 | Schneider et al. | 424/450 |

FOREIGN PATENT DOCUMENTS

DE    36 35 506 A1    4/1988

OTHER PUBLICATIONS

P.L. Ahl et al., Interdigitation–Fusion: A New Method for Producing Lipid Vesicles of High Internal volume *Biochimica et Biophysica Acta*, 1195, 237–244 (1994).

L. Boni et al., The Size Dependence of Interdigitation *Biophysical Journal*, vol. 59, 503 (1991).

H. Komatsu et al., Effect of Unilamellar Vesicle Size on Ethanol–Induced Interdigitation in Dipalmitoylphosphatidylcholine *Chemistry and Physics of Lipids*, 65, 11–21 (1993).

(List continued on next page.)

Primary Examiner—Collamudi S. Kishore
(74) Attorney, Agent, or Firm—Townsend and Townsend and Crew LLP

(57) ABSTRACT

This invention provides methods of loading preformed liposomes by transmembrane permeation induced by alcohols. Solutes loaded into liposomes by this ethanol mediated process include both small nonpolar molecules and larger species, such as proteins and carbohydrates.

20 Claims, 12 Drawing Sheets

OTHER PUBLICATIONS

H. Komatsu et al., Effect of Cholesterol on the Ethanol–Induced Interdigitated Gel Phase in Phosphatidylcholine: Use of Fluorophore Pyrene–Labeled Phosphatidylcholine *Biochemistry*, 30, 2463–2470 (1991).

P. Nambi et al., Studies of the Ethanol–Induced Interdigitated Gel Phase in Phosphatidylcholines Using the Fluorophore, 1,6–Diphenyl–1,3,5–Hexatriene *Biochemistry*, 27, 9175–9182 (1988).

J.L. Ranck et al., Choline and Acetylocholine Induce Interdigitation of Hydrocarbon Chains in Dipalmitoylphosphatidylglycerol Lamellar Phase with Stiff Chains *FEBS Letters*, vol. 143, 171–174 (1982).

E.S. Rowe, Thermodynamic Reversibility of Phase Transitions. Specific Effects of Alcohols on Phosphatidylcholines *Biochimica et Biophysica Acta*, vol. 813, 321–330, (1985).

E.S. Rowe, Comparative Effects of Short Chain Alcohols on Lipid Phase Transitions *Alcohol*, vol. 2, 173–176 (1985).

E.S. Rowe et al., Differential Scanning Calorimetric Studies of Ethanol Interactions with Distearoylphosphatidylcholine: Transition to the Interdigitated Phase *Biochemistry*, vol. 29, 10398–10404 (1990).

E.S. Rowe, Induction of Lateral Phase Separations in Binary Lipid Mixtures by Alcohol *Biochemistry*, vol. 26, 46–51 (1987).

M.J. Ruocco et al., Comparative Study of the Gel Phases of Ether–and–Ester–Linded Phosphatidylcholines *Biochemistry*, vol. 24, 2406–2411 (1985).

S.A. Simon et al., Interdigitated Hydrocarbon Chain Packing Causes the Biphasic Transition Behavior in Lipid/Alcohol Suspensions *Biochimica et Biophysica Acta*, vol. 773, 169–172 (1984).

J.A. Veiro et al., Effect of Alcohols on the Phase Transitions of Dihexadecylphosphatidylcholine *Biochimica et Biohphysica Acta*, vol. 943, 108–111 (1988).

\* cited by examiner

METHOD OF LOADING PREFORMED LIPOSOMES USING ETHANOL

FIELD OF THE INVENTION

This invention relates to the field of liposomes. More particularly this invention relates to the field of loading liposomes or releasing solutes from liposomes by transmembrane permeation.

BACKGROUND OF THE INVENTION

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (non-polar) "tails" of the lipid monolayers orient toward the center of the bilayer while the hydrophilic (polar) "heads" orient towards the aqueous phase.

A variety of liposome types are known and include multilamellar vesicles (MLV's), single unilamellar vesicles (SUV's), large unilamellar vesicles (LUV's), stable plurilamellar vesicles (SPLV's), frozen and thawed multilamellar vesicles (FATMLV's), reversed phase evaporation vesicles (REV's) as described in U.S. Pat. Nos. 5,049,392, 5,204,112 and 5,262,168.

One of the primary uses for liposomes is as carriers for a variety of materials such as drugs, cosmetics, diagnostic reagents, biological materials such as proteins, hormones, antibodies, nucleic acids and polypeptides, and the like.

So far, several methods have been developed for liposome loading. The simplest method of loading is a passive entrapment of a water soluble material in the dry lipid film by hydration of lipid components. The loading efficiency of this method is generally low because it depends on the entrapping volume of the liposomes and on the amount of lipids used to prepare them. Loading efficiency can be increased by the dehydration-rehydration method in which preformed liposomes are dehydrated in the presence of solute and subsequently reconstituted. Disadvantages include heterogenous size, difficult standardization and low reproducibility.

Recently ethanol has been employed to generate interdigitated fusion vesicles (IFV) composed of saturated phospholipids. This method produces large vesicular structures which exhibit large trap volumes (10–20 L/mole) and therefore high trapping efficiencies (P. L. Ahl et al. (1994) "Interdigitation-fusion: a new method for producing lipid vesicles of high internal volume" *Biochimica Et Biophysica Acta* 1195:237–244). It is known that acyl chain interdigitation can be induced by small, amphipathic molecules such as ethanol (F. Zhang et al (1992) "Titration calorimetric and differential scanning calorimetric studies of the interactions of n-butanol with several phases of dipalmitoylphosphatidylcholine" *Biochemistry* 31:2005–2011; E. S. Rowe and T. A. Cutrera (1990) "Differential scanning calorimetric studies of ethanol interactions with distearoylphosphatidylcholine: transition to the interdigitated phase" *Biochemistry* 29: 10398–10404; J. A. Veiro et al. (1988) "Effect of alcohols on the phase transitions of dihexadecylphosphatidylcholine" *Biochimica Et Biophysica Acta* 943:108–111; E. S. Rowe (1987) "Induction of lateral phase separations in binary lipid mixtures by alcohol" *Biochemistry* 26:46–51; S. A. Simon (1984) "Interdigitated hydrocarbon chain packing causes the biphasic transition behavior in lipid/alcohol suspensions" *Biochimica Et Biophysica Acta* 773:169–172), but only for saturated lipids and in the absence of cholesterol. The formation of IFV occurs when small vesicles (<200 nm) are induced to form sheets of interdigitated phase lipid by the addition of 5 M ethanol at temperatures below the gel to liquid crystalline phase transition ($T_c$) of the phospholipid. When the temperature is raised above $T_c$, the sheets spontaneously form large bilayer vesicles which are now stable above or below $T_c$ once ethanol has been removed. It is well known that ethanol can induce an interdigitated organization of phospholipids when it is added to hydrated bilayers composed of saturated phospholipids. However, interdigitation does not occur for unsaturated phospholipids. (P. L. Ahl et al. (1994) "Interdigitation-fusion: a new method for producing lipid vesicles of high internal volume" *Biochimica Et Biophysica Acta* 1195:237–244; H. Komatsu et al. (1993) "Effect of unilamellar vesicle size on ethanol-induced interdigitation in dipalmitoylphosphatidylcholine" *Chemistry & Physics of Lipids* 65:11–21; J. W. Zeng and P. L. Chong (1991) "Interactions between pressure and ethanol on the formation of interdigitated DPPC liposomes: a study with Prodan fluorescence" *Biochemistry* 30:9485–9491; L. L. Herold (1987) "13C-NMR and spectrophotometric studies of alcohol-lipid interactions" *Chemistry & Physics of Lipids* 43:215–225). DPPC has been studied the most in this regard and it has been shown that small DPPC vesicles will collapse in the presence of ethanol to form extended sheets of lipid in an interdigitated state (P. L. Ahl et al. (1994) "Interdigitation-fusion: a new method for producing lipid vesicles of high internal volume" *Biochimica Et Biophysica Acta* 1195:237–244).

More recently another method for liposome loading has involved adding solutes to pre-formed intact liposomes. Typically, higher loading efficiencies are obtained. In this method, conditions are provided under which the substances can penetrate into the vesicle core through its walls; this technique called "transmembrane loading", involves internalizing the substances to be encapsulated into the liposome vesicles after the latter have been formed. A transmembrane chemical potential is employed to drive the substance to be loaded into the liposome. Commonly, the transmembrane potential is created by a concentration gradient which is formed by having differing concentrations of a particular species on either side of the liposomal membrane. Neutralization of the concentration gradient is coupled to flow of the substance being loaded into the liposome. pH gradients (U.S. Pat. Nos. 4,946,683; 5,192,549; 5,204,112; 5,262, 168; 5,380,531), Na+/K+ gradients (U.S. Pat. Nos. 5,171,578; 5,077,056) and $NH_4+$ gradients (U.S. Pat. No. 5,316,771) have been used to load a variety of drugs into liposomes. One limitation of using ion gradients is that the substance being loaded must be an ionizable or protonatable substance. Therefore, the substances loaded by these methods are typically ionizable compounds, often weakly acidic or basic or amphipathic molecules. Other chemical potential driven methods for liposome loading after liposome formation have used a concentration gradient of the solute itself to drive the loading process by employing precursor liposomes with low ionic strength interiors and raising the temperature above the crystal/liquid transition temperature $T_c$ or temporarily disrupting the liposome membrane with shear stresses (U.S. Pat. Nos. 5,393,350; 5,104,661 and 5,284,588). Despite the availability of these methods for liposome loading, it is still desirable to have alternative methods which do not have the limitations of the methods described above. This invention fulfills this and other needs.

SUMMARY OF THE RELATED ART

1. H. Komatsu et al. (1993) "Effect of unilamellar vesicle size on ethanol-induced interdigitation in dipalmitoylphosphatidylcholine" *Chemistry and Physics of Lipids* 65:11–21; discloses that DPPC unilamellar vesicles are capable of becoming interdigitated in the presence of ethanol and that this tendency increases with increasing vesicle size.

2. E. S. Rowe and T. A. Cutrera (1990) "Differential scanning calorimetric studies of ethanol interactions with distearoylphosphatidylcholine: transition to the interdigitated phase" *Biochemistry* 29: 10398–10404; discloses effect of dilution on the ethanol-induced interdigitated state of saturated phosphatidylcholine multilamellar liposomes.

3. Komatsu et al. (1991) "Effect of cholesterol on the ethanol-induced interdigitated gal phase in phosphatidylcholine: use of fluorophore pyrene-labeled phosphatidylcholine" *Biochemistry* 30:2463–2470; discloses that 20 mol % cholesterol prevents the induction of interdigitation by ethanol in 1,2 DPPC multilamellar liposomes.

4. S. A. Simon (1984) "Interdigitated hydrocarbon chain packing causes the biphasic transition behavior in lipid/alcohol suspensions" *Biochimica Et Biophysica Acta* 773:169–172; discloses the interdigitated gel phase induced by ethanol in DPPC and DSPC vesicles.

5. E. S. Rowe (1987) "Induction of lateral phase separations in binary lipid mixtures by alcohol" *Biochemistry* 26:46–51; discloses the induction of the interdigitated state by ethanol in mixed binary phosphatidylcholine (PC)/phosphatidylethenolamine (PE) vesicles.

6. U.S. Pat. No. 5,393,530, Schneider et al., Feb. 28, 1995, *Method for Making Liposomes of Enhanced Entrapping Capacity Toward Foreign Substances to be Encapsulated*; discloses loading of liposomes containing very dilute solutions of low osmolality by incubation at temperatures greater than the lipid transition temperature.

7. U.S. Pat. No. 4,994,213, Aitcheson et al., Feb. 19, 1991, *Method of Preparing Lipid Structures*; discloses forming liposomes by dissolving lipids in an organic solvent in the presence of a solute to be entrapped and gradually removing organic solvent by reverse osmosis.

8. U.S. Pat. No. 4,952,408 discloses using ethanol as a solvent during liposome production.

9. U.S. Pat. No. 4,877,561, Iga et al., Oct. 31, 1989, *Method of Producing Liposome*; discloses that liposomes with an increased drug trap can be prepared by adding a readily volatile organic solvent to a drug-containing liquid with liposomes dispersed therein to cause gel formation and then removing said organic solvent by evaporation.

10. U.S. Pat. No. 4,814,270, Piran, Mar. 21, 1989, *Production of Loaded Vesicles*; discloses vesicles having a material encapsulated therein are produced by placing an "empty" vesicle in a liquid including a material to be encapsulated and perturbing the vesicle, preferably by passage through a porous material.

11. U.S. Pat. No. 4,683,092, Tsang, Jul. 28, 1987, *Capsule Loading Technique*; discloses porous capsule loading by preparing deflated, dehydrated capsules by sequential washing with increasing amounts of ethanol and then hydrating the capsules in a solution containing the substance to be encapsulated.

12. U.S. Pat. No. 4,389,330 to Tice et al., Jun. 21, 1983, *Microencapsulation Process*; discloses using ethanol as a solvent during liposome production.

13. U.S. Pat. No. 4,235,871, Papahadjopoulos et al., Nov. 25, 1980, *Method of Encapsulating Biologically Active Material in Lipid Vesicles*; discloses a method for forming loaded liposomes by providing a mixture of lipid in organic solvent and an aqueous mixture of the material for encapsulation, emulsifying the provided mixture, removing the organic solvent and suspending the resultant gel in water.

14. U.S. Pat. No. 4,224,179; discloses using ethanol as a solvent during liposome production.

15. German Patent No. DE 3635506 A1, Bartels et al., Apr. 28, 1988, *Antrag auf Nichtnennung*; discloses loading active ingredients into preformed liposomes by temporarily increasing membrane concentration by adding a low concentration of detergent.

SUMMARY OF THE INVENTION

This invention provides a method of loading liposomes with a solute without causing vesicular collapse. The method comprises:

combining an aqueous solution having liposomes dispersed therein with the solute and an organic solvent which increases the membrane permeability of the liposomes to the solute, whereby the solute enters the liposome by transmembrane permeation, and diluting the concentration of the organic solvent thereby decreasing the membrane permeability of the liposome to the solute and trapping the solute in the liposome to provide a liposome loaded with solute.

The invention also provides a method of changing the concentration of a solute in a liposome by increasing the membrane permeability of the liposome to the solute while maintaining the liposome at a substantially similar size. The method comprises:

providing a dispersion of liposomes and the solute, wherein the concentration of the solute in the liposome and outside the liposome are different, adding an organic solvent which increases the membrane permeability of the liposome to the solute, whereby the solute enters or leaves the liposome by transmembrane permeation, provided the solute concentrations in and outside the liposome remain different, thereby changing the concentration of the solute in the liposome.

Another advantage of the present invention is that the liposome size remains substantially unaltered during the membrane permeation process. The method is of particular value for increasing membrane permeation to and loading solutes with a low net charge or low charge to mass ratio.

Preferably, the organic solvent is an alcohol, such as ethanol, and the liposome is made from a phospholipid, preferably an unsaturated phospholipid. The method is of particular value for loading large unilamellar liposomes.

DETAILED DESCRIPTION OF THE PREFERRED EMBODIMENT

Figure 1:
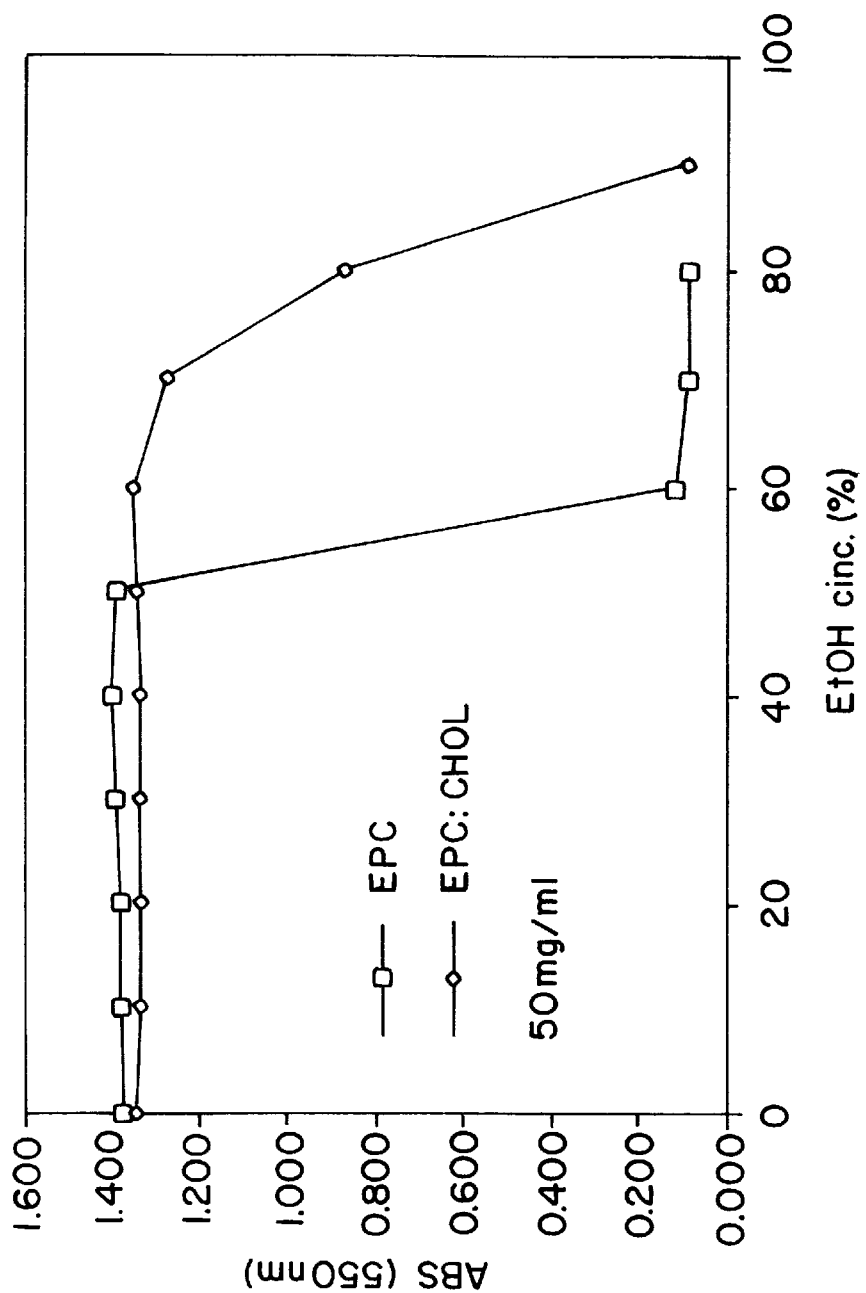
FIG. 1 shows the solubilization of phospholipid vesicles by ethanol. The absorbance at 550 nm of 100 nm EPC (open square) and EPC/cholesterol (open diamond) vesicles at a concentration of 50 mg/ml in various concentrations of ethanol is shown.

As described earlier this invention relates to the loading of liposomes. In particular, this invention provides a method of loading liposomes with a solute without causing vesicular collapse. Vesicular collapse refers to the process whereby the liposomal membrane loses its structural integrity and either "dissolves" into the medium or reorganizes into large "sheets" causing the size homogeneity of the system to be lost. The method comprises:

combining an aqueous solution having liposomes dispersed therein with the solute and an organic solvent which increases the membrane permeability of the liposomes to the solute, whereby the solute enters the liposome by transmembrane permeation, and diluting the concentration of the organic solvent, thereby decreasing the membrane permeability of the liposome to the solute and trapping the solute in the liposome, to provide a liposome loaded with solute. Preferably, the organic solvent is an alcohol and is added to a mixture of the solute and liposomal dispersion.

Unlike the ion gradient driven methods described earlier, the alcohol loading process is not active, so that the solute is not accumulated against a concentration gradient. The alcohol temporarily enhances the permeability of the vesicles, without substantially altering or changing their size, so that solutes added to the extra-liposomal space equilibrate with the internal encapsulated space. The liposomal membranes retain their structural integrity and do not either "dissolve" or reorganize into large "sheets". Therefore, the size homogeneity of the liposomal carrier system is retained. Subsequent dilution returns the permeability barrier to its normal level, thus permanently trapping solute at a concentration equivalent to the total solute concentration before dilution. Dilution may also be effected prior to complete solute equilibration between the external and interior spaces if it is desirable to trap solute at some intermediate concentration less than the external solute concentration before dilution. Similarly, solutes trapped in liposomes can be released into the extraliposomal space by increasing the membrane permeability. This release can be effected up to the point where the solute concentration in the extraliposomal space equals the concentration of solute remaining in the liposome.

This loading procedure is independent of the method used to prepare the unloaded liposomal preparation. Thus, the liposomes may be prepared as MLV, by solvent injection, including lipid hydration, reverse evaporation, freeze drying by repeated freezing and thawing, and regardless of whether the lipid film is thin or thick, though the thin lipid film is preferred. The method works particularly well for unilamellar vesicles, small unilamellar vesicles (SUV), small liposomes prepared by using a French pressure cell, i.e., by passing MLV through a small orifice under high pressure, by solvent injection methods, with solvents such as ethers and alcohols.

Similarly the method will also work for large unilamellar vesicles (LUV), stable plurilamellar vesicles (SPLV) or for oligolamellar vesicles (OLV) whether prepared by detergent removal using dialysis, column chromatography, bio beads SM-2, by reverse phase evaporation (REV), or by formation of intermediate size unilamellar vesicles by high pressure extrusion. *Methods in Biochemical Analysis*, 33:337 (1988). Liposomes made by all these and other methods known in the art can be used in practicing this invention, though large unilamellar vesicles are generally preferred. These methods are described in U.S. Pat. Nos. 4,235,871; 4,241,046; 4,529,561; 4,737,323; and 4,752,425.

The liposomes useful in the current invention may be formed from a variety of vesicle-forming lipids, including dialiphatic chain lipids, such as phospholipids, diglycerides, dialiphatic glycolipids, single lipids such as sphingomyelin and glycosphingolipid, cholesterol and derivatives thereof, alone or in combinations and/or with or without liposome membrane rigidifying agents. Liposomes useful in practicing this invention can be prepared from carboxylic acid diesters of aliphatic triols and higher polyols such as glycerol, sorbitol, mannitol and the like, with glycerol being preferred, in which the ester moieties are derived preferably from ethylenically unsaturated aliphatic monocarboxylic acids (long chain fatty acids) having at least 14 to about 30 carbon atoms such as palmitoleic, oleic, linolenic, linoleic, myristoleic and arachidonic acid. The liposomes may also contain stabilizers and antioxidants such as vitamin E, vitamin C, glutathione, butylated hydroxyanisole, butylated hydroxytoluene and the like.

As defined herein, "phospholipids" include phosphatidic acid (PA), and phosphatidyl glycerols (PG), phosphatidylcholines (PC), phosphatidylethanolamines (PE), phospatidylinositols (PI), phosphatidylserines (PS), and phosphatidyl-choline, serine, inositol, ethanolamine lipid derivatives such as egg phosphatidylcholine (EPC), soy phosphatidylcholine, partially hydrogenated egg phosphatidylcholine (PHEPC), bovine liver phosphatidyl choline, dipalmitoylphosphatidylcholine (DPPC), dioleoylphosphatidylcholine (DOPC), distearoyl phosphatidylserine, dilinoleoyl phosphatidylinositol, and mixtures thereof. They may be unsaturated lipids and may be naturally occurring or synthetic. The individual phosphatidic acid components may be symmtrical, i.e. both acyl residues are the same, or they may be unsymmetrical, i.e., the acyl residues may be different. The liposomes used herein may be made from mixtures of lipids. Generally, the liposome will have at least 1%, typically at least about 10%, preferably at least about 50% and more preferably at least about 90% of an unsaturated lipid.

In a number of embodiments of the present invention, a steroidal component may be a constituent of the liposome. Cholesterol exhibits a specific interaction with phospholipids. In membranes composed of unsaturated phospholipids, the presence of cholesterol restricts acyl chain motion and increases membrane thickness. On the other hand, the interaction of cholesterol with saturated phospholipids prevents the formation of the gel state and tends to eliminate the gel to liquid crystalline phase transition (P. L. Yeagle et al. (1990) "Cholesterol dynamics in membranes" *Biophysical Journal* 57:413–424; R. A. Demel and B., de Kruijff (1976) "The function of sterols in membranes" *Biochimica Et Biophysica Acta* 457:109–132). Representative steroids in addition to cholesterol include lanosterol, cholestanol, coprostanol, ergosterol and the like. In addition, polyethylene glycol derivatives of cholesterol (PEG-cholesterols), as well as organic acid derivatives of sterols, e.g., cholesterol hemisuccinate (CHS) may be used, in combination with any of the above lipids. Generally, the effect of added cholesterol is to decrease the organic solvent induced membrane permeability with unsaturated lipids and to increase membrane permeability with saturated lipids. However with saturated lipids significant vesicle fusion is observed.

The size of the liposomes used is not critical to the invention and liposomes ranging in size from the submicron range up to and greater than 250 microns can be used. The desired size will be typically controlled by factors other than the fact the organic solvent induced membrane permeation method is being used, such as, for example, the size that is preferred for the ultimate end use of the loaded liposome, whether it be a pharmaceutical or cosmetic formulation. The liposomes are frequently about 50 nm to 500 nm in diameter, preferably about 75 nm to 200 nm in diameter, more preferably about 100 nm in diameter. Since vesicle size remains effectively unchanged during this procedure, the present invention conveniently allows one to use preformed unloaded liposomes which have been size fractionated by extrusion procedures and the like which may have been incompatible with the presence of the solute in the liposome.

The organic solvent is generally a polar solvent such as an alcohol, a glycol, an ether, dimethoxyethane, acetone, chloroform, dimethyl sulfoxide and the like which is capable of increasing the membrane permeability of the liposome without causing vesicular collapse or substantially altering the size of the liposome. In this context "substantially altering" refers to a change of greater than about 20%, preferably about 10% in the liposome diameter. Mixtures of organic solvents can be used. Some liposome fusion may occur, provided large scale reorganization of the vesicles which destroy the size homogeneity of the liposome distribution does not occur. Hydrophilic, low molecular weight water miscible alcohols with less than 10 carbon atoms, preferably less than 6 carbon atoms are preferred. Typical alcohols used in this invention are methyl alcohol, ethyl alcohol, n-propyl alcohol, isopropyl alcohol and n-butyl alcohol, sec-butyl alcohol and tert-butyl alcohol, pentanol and ethylene glycol and propylene glycol.

Generally, the organic solvent is added to the liposomes up to about 10% (v/v), preferably up to about 20%, more preferably up to about 30%. At these concentrations mean vesicle diameter remains substantially unchanged (i.e., changes by less than about 30%, preferably less than about 20%, more preferably less than about 10%), but membrane permeability is increased by $10^6$ to $10^7$ fold, or at least $10^4$ fold over the permeability in the absence of solvent for small solutes (molecular weights less than about 1000). Consequently, solutes equilibrate across the vesicle membrane in seconds rather than months to years. High molecular weight solutes, for example macromolecular solutes such as proteins, enzymes, polysaccharides and the like also exhibit increased membrane permeation rates in the presence of an organic solvent, though typically the increase is not as dramatic as with low molecular weight solutes. With high molecular weight solutes (>1000 daltons, typically greater than 10,000 daltons and as high as 1 million daltons) increases in permeation rates of as much as 1000 fold to 10,000 fold can be obtained.

At organic solvent concentrations substantially in excess of 30%, vesicle size increases dramatically and vesicle fusion and membrane solubilization occur. Vesicle fusion is not required for solute equilibration, since EPC vesicles maintained in 30% ethanol show no signs of fusion but have completely lost their ability to retain entrapped sucrose. Consequently this invention provides liposomes which are structurally stable and maintain their size over a range of ethanol concentrations that are sufficient to substantially increase membrane permeability to nonpolar species such as for example but not limited to, sucrose, carbohydrates, oligosaccharides, polysaccharides, peptides and the like. Nonpolar species are generally those that are substantially uncharged under the loading conditions. Preferably, the net charge on the molecule will be about 0–2, more preferably approximately zero. However, higher net charges can be tolerated if the charge is sufficiently diffuse.

One skilled in the art will recognize that the organic solvent may be present admixed with the liposomes before the addition of the solute to be loaded. Without being bound by any particular theory, it is believed that the organic solvent perturbs the liposomal membrane to an extent sufficient to increase the permeability of the membrane to the solute thus allowing traversal of the solute into, across and through the membrane. This diffusion of solute through the membrane will continue until the concentration gradient of solute between the interior and exterior of the liposome is removed. Therefore, it is apparent that the order in which the liposome, solute and organic solvent mixture is generated from its constituent parts is not critical to the practice of the invention.

Since the method rests on the presence of a concentration gradient of solute between the liposome and its exterior, it will also be apparent that the transmembrane permeation of solute will continue as long as this gradient exists. Therefore, any mechanism which "removes" the solute from the "low concentration" side of the membrane, by chemical reaction, adsorption and the like, will act to preserve the gradient and drive continued permeation of the solute. For example, if the solute is an enzyme substrate and is turned over by enzyme which is present only in the "low concentration" side of the membrane, transmembrane permeation of the solute can continue until the enzyme no longer turns over solute and the free solute concentrations on both sides are equal. Another example occurs when the solute is trapped by a binding substance, such as an antibody, which thereby reduces the effective concentration of the free solute, thus preserving the concentration gradient of free solute between the two sides of the membrane.

As should be apparent, the quantity of organic solvent used is such that the liposomal membrane is rendered permeable to the solute without permanently or irreparably disrupting or destroying the liposome. This is generally evidenced by the fact that liposome size remains substantially constant during the process and that liposomal fusion is not observed until much higher concentrations of organic solvent are used. The liposome can be resealed and rendered impermeable to the solute either when the solute concentrations in and outside the liposomes are equalized or at some earlier point in the process.

The organic solvent-induced transmembrane permeation disclosed by the present invention does not require elevated temperatures. In particular, there is no necessity, unlike some of the methods of the prior art, that the loading process be practiced at temperatures at or in excess of the $T_c$ of the liposomal membrane. Therefore, it is possible to employ in this invention heat-labile solutes which might otherwise be degraded. Loading or release of solutes can therefore be accomplished at room temperature or lower, such as at 4 degrees C.

The ability to temporarily eliminate, or drastically reduce, the permeability barrier of vesicles without altering their size is of interest because it means that solutes added to a suspension of vesicles in ethanol will rapidly cross the membrane and equilibrate with the internal aqueous space. As described above, the permeability coefficient for sucrose is $10^6$ to $10^7$ fold greater for EPC vesicles in 30% ethanol compared to buffer alone. Consequently, in ethanol, sucrose equilibrates across the vesicle membrane in seconds rather than months to years. However, this process is not of practical use with respect to loading solutes (such as drugs) into preformed vesicles unless the permeability barrier can be restored rapidly enough to effectively trap solute.

In order for this method to effectively trap solutes after membrane permeation, the permeability barrier must be restored rapidly enough to prevent solute re-equilibration. Generally this is accomplished by diluting the organic solvent by at least a factor of at least about two, preferably by a factor of ten, more preferably by a factor of at least twenty. For example, when sucrose is loaded into liposomes at a 30% ethanol concentration, diluting the ethanol concentration to about 10–15% was sufficient to reduce the permeability coefficient by several orders of magnitude, thus effectively trapping the contents of the liposome in the liposome. Dilution can be accomplished by any available means ranging from the direct addition of additional aqueous media, flash evaporation and gel filtration, the latter being particularly effective at removing substantially all of the organic solvent. Any other method of rapidly removing or reducing the concentration of the organic solvent, such as, for example, selective absorption may also be used.

The type of buffer in which the liposomes are initially dispersed is not critical to the invention. Thus, unlike some of the methods disclosed in the prior art, there is generally no requirement that the aqueous medium in which the liposomes are suspended be of low ionic strength or osmolality. Typical buffers include NaCl, KCl, sodium or potassium phosphate, carbonate, bicarbonate, borate, tris, HEPES (N-2-hydroxyethyl-piperazine-N'-2-ethanesulfonic acid), MES (2-N-morpholinoethanesulfonic acid), PIPES (Piperazine-N,N'-bis(2-ethanesulfonic acid)) and the like.

The pH is whatever is required to maintain liposomal integrity and can range from 2 to 11 and is typically about 6 to 8.

A variety of solutes can be induced to cross the liposomal membrane by transmembrane permeation and loaded into liposomes using the solvent loading method disclosed herein. Unlike the ion gradient methods disclosed in the prior art, the solvent loading method is not limited to ionizable solutes. Thus, uncharged or neutral species or substances that are not capable of being induced to carry a charge by protonation, cation or anion binding and the like, can be loaded into the liposomes. The transmembrane permeation of the solute can be simply accomplished by adding an organic solvent to an aqueous dispersion of liposome and solute, waiting for the appropriate length of time, i.e., for equilibration to occur or until the solute concentration in the liposome reaches the desired level, and diluting out or removing the organic solvent. As was explained previously, the order of addition is unimportant and the solute can be added to a mixture of liposome and organic solvent. Alternatively, a mixture, suspension or solution and the like of the solute in the organic solvent can be added to the liposomes. Drugs, diagnostics, hormones, carbohydrates, oligo- and polysaccharides, vitamins, steroids, pesticides, plant nutrients or growth factors, proteins, antibodies, enzymes, chromophores, fluorophores, enzyme inhibitors and activators, cosmetics and the like may be loaded into the liposomes. Generally, highly negatively charged species such as polynucleotides do not cross liposomal membranes permeabilized by the solvent technique disclosed herein and are loaded with low levels of efficiency. This allows selective release or entrapment of neutral species in the presence of highly charged species by increasing membrane permeability by the solvent loading methods disclosed herein. It will be recognized that the charge on a molecule can be adjusted by by a variety of methods, including but not limited to, varying the pH of the medium, providing counter ions which diffuse the charge, covalent modification. For example, charged oligonucleotides can be converted to less highly charged analogs which continue to display biological activity by methylation or conversion to the corresponding phosphorothioates, methylphosphonates and the like.

Diagnostic reagents that may be used in this invention include radioactive materials, enzymes, chemiluminescent substances, spin labels, chromogens including fluorescent dyes and visible dyes, pH indicators (e.g., pyranine) and the like.

Representative enzymes that may be loaded into liposomes or induced to cross the liposomal membrane by the organic solvent mediated increase in membrane permeability include, horseradish peroxidase, lactase, alkaline phosphatase, diaphorase, beta-galactosidase, ribonuclease, trypsin, chymotrypsin, amylase, esterase, phospholipase and the like. Representative drugs that may be used likewise in the present invention include anticancer agents such as doxorubicin and amphotericin, anti-inflammatory agents such prednisone, cortisone and the like, antihistamines such as chlorpromazine, antidepressants, anticonvulsants, antiemetics, alkaloids such as vincristine and vinblastine, analgesics, tranquilizers etc. Other representative solutes that may be used in the present invention are disclosed in U.S. Pat. No. 4,389,330, col. 5 and 6 and U.S. Pat. No. 5,171,578, col. 6. Antibiotics such as gentamicin and the like, and other aminoglycosides, penicillins, cephalosporins, fluoroquinolones such as ciprofloxacin may also be loaded by the methods disclosed herein. Generally, the loading of all drugs that can cross the vesicle bilayer in the presence of up to 30% ethanol are contemplated by this invention. Such drugs can be readily identified by encapsulating the drug of interest and then adding ethanol to see if the drug is released from the vesicle. One will recognize that this method of loading and/or release is therefore independent of any particular molecular characteristic of the drug (e.g., charge, molecular weight, etc.).

EXAMPLES

Abbreviations

QELS—Quasielastic light scattering

MATERIALS AND METHODS

Lipids and Chemicals

Egg phosphatidylcholine (EPC) was obtained from Nichiyu Liposome (Tokyo, Japan). Dipalmitoylphosphatidylcholine (DPPC) was purchased from Avanti Polar Lipid (Birmingham, Ala.). [$^{14}$C]sucrose, [methoxy-$^3$H]inulin and [$^3$H]dextran were obtained from New England Nuclear (Mississauga, ON). All other chemicals were obtained from Sigma (St. Louis, Mo.) and were of analytical grade.

Vesicle Preparation

Lipid films were made by drying chloroform solutions of lipids under a stream of nitrogen followed by exposure to high vacuum for approximately 2 h. Large multilamellar vesicles (MLV) were prepared by hydrating (vortex mixing) the dry lipid film in 150 mM NaCl, 20 mM Hepes (pH 7.0). EPC and EPC/cholesterol (55:45 mol ratio) were hydrated at 50° C. Lipid concentrations of 50 mg/H were routinely employed. The MLV were frozen in liquid nitrogen and thawed in warm water at the same temperature used for hydration. Samples were subjected to five freeze-thaw cycles which has been shown to increase the trapped volume of MLV and promote the equilibration of solute across internal lamellae (L. D. Mayer et al. (1985) "Solute distributions and trapping efficiencies observed in freeze-thawed multilamellar vesicles" *Biochimica Et Biophysica Acta* 817:193–196). Large unilamellar vesicles (LUV) were prepared by extrusion of MLV through polycarbonate filters (100 mn pore size) as described by Hope et al. (M. J. Hope (1985) "Production of large unilamellar vesicles by a rapid extrusion procedure. Characterization of size distribution, trapped volume and ability to maintain a membrane potential" *Biochimica Et Biophysica Acta* 812:55–65) using a thermobarrel Extruder™ (Lipex Biomembranes, Vancouver, BC). The size distribution of vesicles was determined by quasi-elastic light scattering analysis (M. J. Hope et al. (1986) "Generation of multilamellar and unilamellar phospholipid vesicles" *Chemistry & Physics of Lipids* 40:89–107) employing a Nicomp particle sizer (Pacific Scientific, NM).

Determination of Trapped Volumes and Permeability Coefficient

Trapped volumes of vesicles were determined using [$^{14}$C] sucrose, [methoxy-$^3$H]inulin and [$^3$H][dextran as markers for the internal aqueous space. Phospholipid was hydrated in the presence of trace amounts of the markers ($1\mu$ Ci/ml). After extrusion, untrapped marker was removed by gel filtration column chromatography. Radioactivity was measured using a Beckman Model 3801 liquid scintillation counter and phospholipid concentrations were determined colorimetrically using a modification of the method described by Fiske and SubbaRow (C. H. Fiske and Y. SubbaRow (1925) *J. Biol. Chem.* 66:375–400). Trapped volumes were calculated from the specific activity of markers and expressed as liters of aqueous trapped volume per mole of total lipid (L/mole). Permeability coefficients were calculated from the rate at which sucrose was either released from or entered vesicles, that were incubated in different concentrations of ethanol, according to the method described by Toyoshima and Thompson (Y. Toyoshima and T. E. Thompson (1975) "Chloride flux in bilayer membranes: chloride permeability in aqueous dispersions of single-walled, bilayer vesicles" *Biochemistry* 14:1525–1531). All ethanol concentrations are referred to as % (v/v). A number of experiments were performed to demonstrate that as soon as aliquots of vesicles were added to the top of mini gel filtration columns ethanol was removed from the vesicle membrane so rapidly that the normal permeability barrier returned before solutes such as sucrose could leak. Some of these experiments are discussed in the Results.

Freeze-Fracture Electron Microscopy

Vesicle preparations were mixed with glycerol (25% v/v) and frozen from 20° C. in a freon slush suspended in liquid nitrogen. Samples were fractured and replicated employing a Balzers BAF 400D apparatus and micrographs of replicas were obtained using a Jeol JEM-1200 EX electron microscope.

General Methods

Typically a 50% (v/v) solution of ethanol in buffer was added to a suspension of EPC, EPC/cholesterol, DPPC and DPPC/cholesterol vesicles (containing [$^{14}$C]sucrose) in a volume ratio chosen to produce the desired final ethanol concentration (usually between 0 and 30% v/v). In experiments designed to demonstrate that the ethanol effect was reversible, samples taken to 30% v/v ethanol were dialyzed against the appropriate ethanol/buffer concentration (30% to 0%). The permeability of LUV to sucrose was determined two ways, either by measuring the rate at which sucrose entered vesicles or the rate at which sucrose was released from vesicles. Entry was measured by adding [$^{14}$C]sucrose to the external medium and removing 100 $\mu$l aliquots for gel filtration at different times. The aliquots were applied to mini sephadex G50 m columns prepared in 1 ml tuberculin syringes which were subsequently centrifuged at 3000 rpm for approximately 2 m to separate free sucrose from encapsulated. The phospholipid concentration of the column eluant was determined by standard phosphate assay. For release experiments vesicles were made in the presence of [$^{14}$C] sucrose and untrapped marker removed before ethanol was added. Aliquots were removed and subjected to gel filtration as described above to measure the amount of sucrose lost. Permeability coefficients were calculated from the rates of entry or leakage.

RESULTS

I. Effect of Ethanol on Vesicle Size and Release of Sucrose

EPC vesicles were mixed with ethanol solutions so that the final concentration was always 50 mg total lipid/ml. Absorbance at 550 nm of 100 nm EPC vesicles and EPC/cholesterol vesicles at a concentration of 50 mg/ml in various concentrations of ethanol was measured. Approximately 60% ethanol was sufficient to completely solubilize EPC vesicles. This is shown in FIG. 1 where the light scattering from a suspension of 100 nm vesicles, measured as the absorbance at 550 nm, drops precipitously on going from 50% to 60% (ethanol in buffer, v/v) as the suspension changes from translucent to clear. The presence of cholesterol delays clarification until vesicles are suspended in solutions of 90% ethanol.

Figure 2:
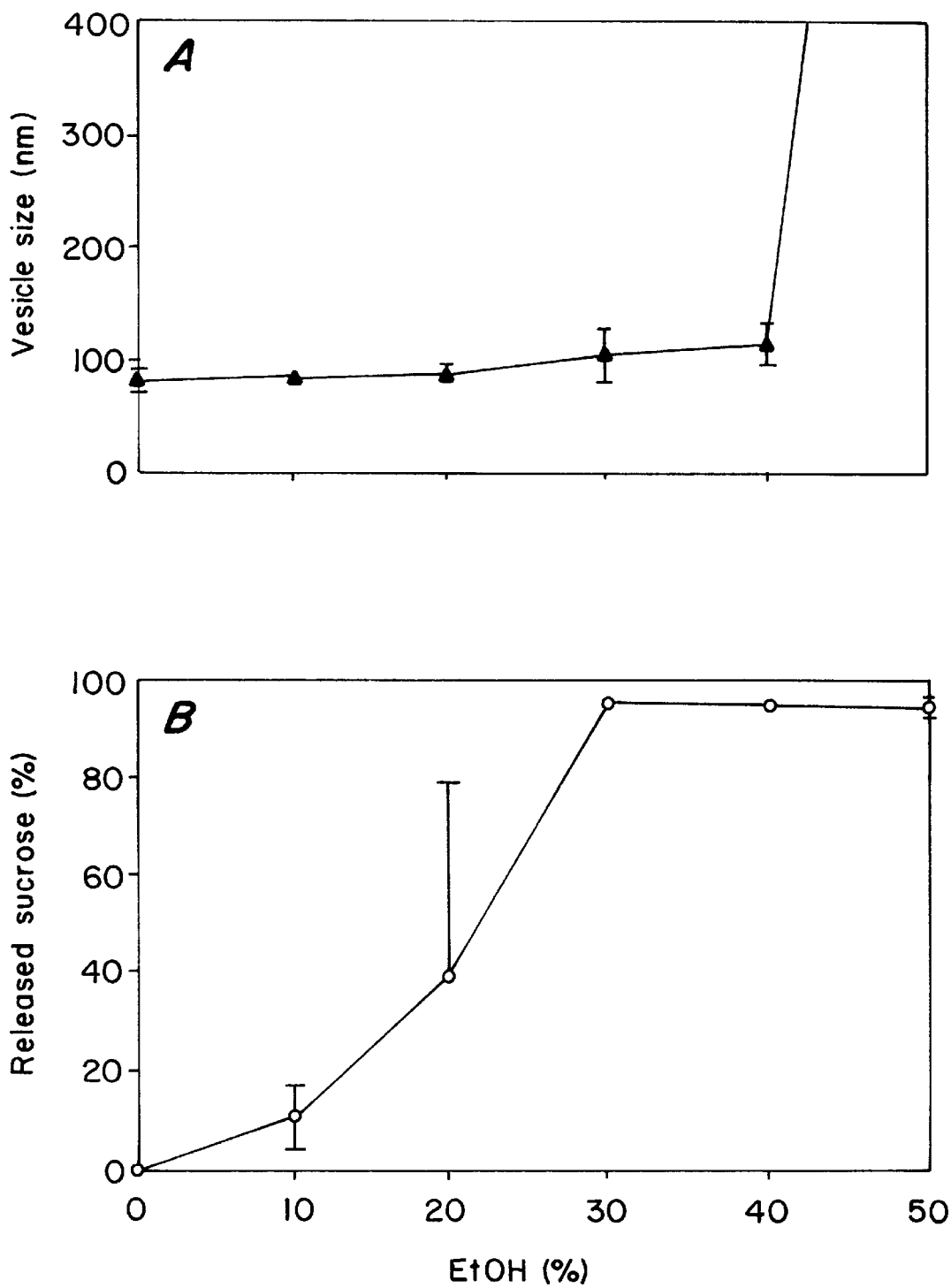
FIG. 2 shows the effect of ethanol on EPC vesicles: (A) vesicle size and (B) permeability to sucrose.

EPC vesicles, sized by extrusion through 100 nm pore size filters and containing [$^{14}$C]sucrose (1 mM), were incubated for 30 m at 25° C. in the buffer/ethanol mixtures indicated in FIG. 2. Aliquots were removed and the mean diameter determined by QELS analysis. The % release of sucrose was measured following gel filtration as described in Methods.

Although EPC vesicles were solubilized by concentrations of ethanol above 50% (v/v) it was surprising to find that ethanol did not significantly effect the mean vesicle diameter until ethanol concentrations of 40% or greater. FIG. 2A shows that EPC LUV prepared by extrusion through 100 nm pore size filters (M. J. Hope (1985) "Production of large unilamellar vesicles by a rapid extrusion procedure. Characterization of size distribution, trapped volume and ability to maintain a membrane potential" *Biochimica Et Biophysica Acta* 812:55–65) maintained a mean diameter of approximately 100 nm for 30 m at 25° C. in ethanol concentrations up to and including 40% (v/v). At 50% ethanol, however, vesicle size increases dramatically to >1 Am, which is consistent with massive vesicle fusion prior to solubilization. Furthermore, the ability of the vesicle membrane to retain sucrose was almost completely eliminated at ethanol concentrations well below that which induced fusion. The amounts of encapsulated sucrose released from vesicles following the 30 m incubation are presented in FIG. 2B and show that between ethanol concentrations of 10 to 30%, the permeability barrier to sucrose decreases significantly, and above 30% all of the entrapped sucrose is lost within the 30 m period. Consequently, EPC vesicles are structurally stable and maintain their size over a range of ethanol concentrations that are sufficient to substantially increase membrane permeability to sucrose.

Figure 4:
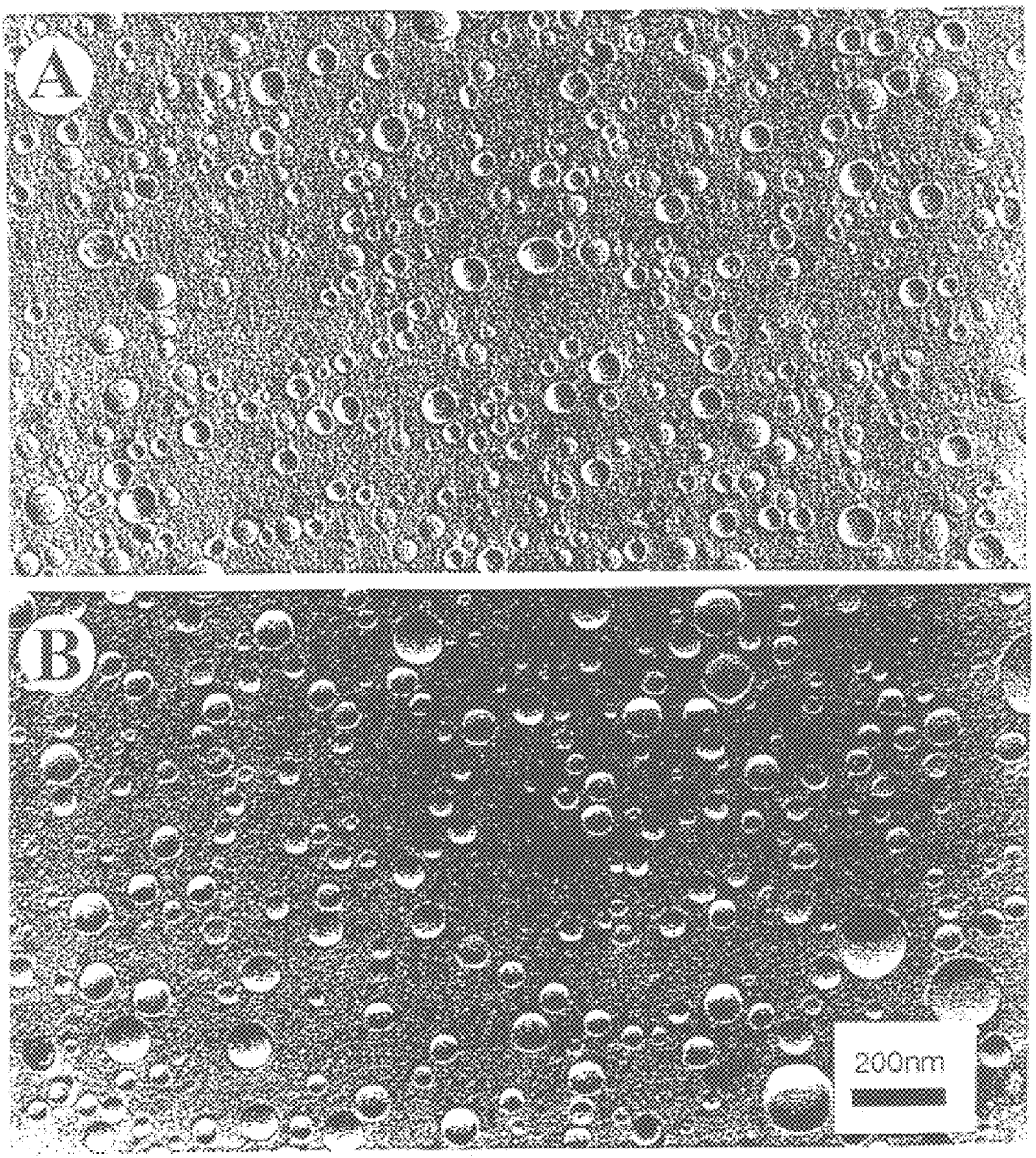
FIG. 4 shows freeze-fracture micrographs of 100 nm EPC vesicles: (A) 0% ethanol and (B) 30% ethanol.

This is supported by the freeze-fracture micrographs presented in FIG. 4. FIG. 4A shows EPC vesicles (100 nm) before mixing with ethanol. FIG. 4B shows EPC vesicles in 30% (v/v) ethanol. These show that overall vesicle structure does not change in the presence of 30% ethanol. The permeability coefficient for sucrose in the vesicles shown in the vesicles shown in panel A was at least six orders of magnitude smaller than for the vesicles shown in panel B.

II. Encapsulation of Sucrose in Preformed Vesicles

EPC vesicles were mixed with ethanol/buffer to give suspensions with a final ethanol concentration of 0, 10, 20 and 30% (v/v). [$^{14}$C]sucrose was added to a total concentration of 1 mM and aliquots removed at different time intervals to determine how much sucrose had penetrated the vesicles. From the rate of sucrose uptake the permeability coefficient for the sugar was calculated at each ethanol concentration. In order to demonstrate the effect was reversible, vesicles in 30% ethanol were dialyzed overnight against 20, 10 and 0% ethanol buffer and the rate of sucrose penetration into the vesicles determined. The data are shown in FIG. 3.

Figure 3:
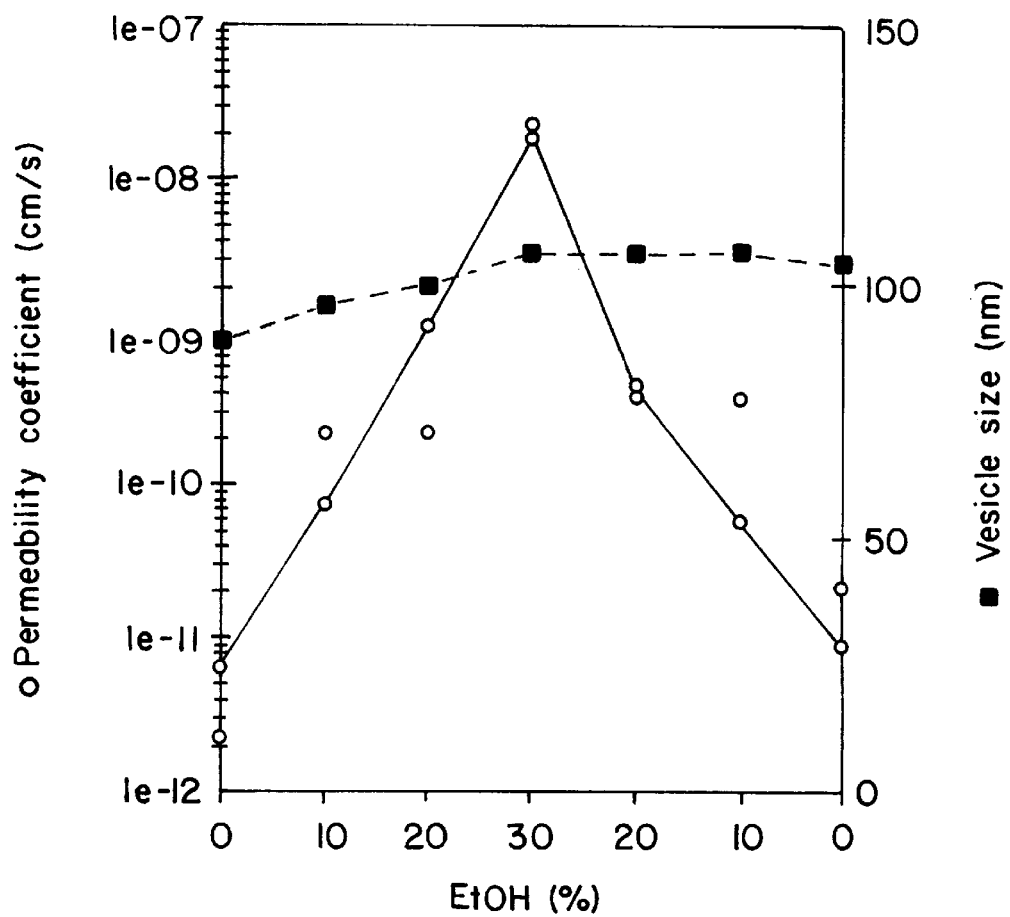
FIG. 3 shows the reversible effect of ethanol on the permeability coefficient for sucrose through EPC vesicle membranes.

The data in FIG. 3 show that even a two fold dilution of vesicles from 30% ethanol to 10–15% is sufficient to reduce the permeability coefficient by several orders of magnitude therefore trapping encapsulated contents. In the experiments designed to measure the influx of sucrose, 100% equilibration took place based on the known trap volume of 100 nm vesicles. These vesicles had been passed down a gel filtration column, a process known to remove ethanol (M. J. Hope et al. (1986) "Generation of multilamellar and unilamellar phospholipid vesicles" *Chemistry & Physics of Lipids* 40:89–107). The sucrose isolated with the vesicles was equivalent to the sucrose concentration before dilution. Therefore, very little of the internal sucrose contents had leaked during ethanol extraction. In order to test this further, vesicles were made in the presence of [$^{14}$C]sucrose (1 mM), so that labelled sugar was present in both the internal (encapsulated) and external aqueous spaces. Ethanol was added to the vesicle suspension to concentrations from 0–30% and after 30 m the alcohol was extracted by adding 100 μl aliquots to the top of mini gel filtration columns followed by centrifugation to isolate the vesicles. This technique employs 1 ml tuberculin syringes packed with sephadex which have been washed by centrifugation with 100 μl aliquots of buffer. Consequently, the sephadex is fully hydrated but does not contain excess buffer and any sample added is immediately drawn into the column by capillary action. Therefore this method results in a very rapid dilution/extraction of ethanol.

The amount of sucrose trapped in the vesicles was determined. From the amount of sucrose trapped in the eluted vesicles, the encapsulated aqueous volume was calculated and compared to theoretical values for the known vesicle size as well as to values determined experimentally in the absence of ethanol. The data showed trap volumes in the range of 2.0–3.0 L/mole when calculated from the sucrose encapsulated in the presence of 30% ethanol. The exact volume varied with the mean diameter of the population, but this range compares very well with the theoretical encapsulated volume of a homogeneous population of 100 nm vesicles, which is approximately 2.7 L/mole for EPC (M. J. Hope (1985) "Production of large unilamellar vesicles by a rapid extrusion procedure. Characterization of size distribution, trapped volume and ability to maintain a membrane potential" *Biochimica Et Biophysica Acta* 812:55–65). It is interesting to note that when EPC vesicles are prepared by normal extrusion through 100 nm pore size filters they exhibit lower trap volumes typically on the order of 1.5 L/mole. It has recently been shown that this is due to the extrusion process which produces "oblong" vesicles with a reduced volume/surface ratio compared to a sphere (M. L. Bui et al. (1993) "Osmotic properties of large unilamellar vesicles prepared by extrusion" *Biophysical Journal* 64:443–453). The elongated shape is maintained by osmotic forces, but if these are collapsed vesicles revert to spheres with maximum volume/surface ratio and trapped volumes of approximately 2.0 L/mole for a vesicle population similar to the one described here (M. L. Bui et al. (1993) "Osmotic properties of large unilamellar vesicles prepared by extrusion" *Biophysical Journal* 64:443–453). The results shown here are consistent with ethanol collapsing the permeability barrier and allowing osmotic equilibration to occur.

III. Lipid Composition and Vesicle Stability

Figure 5:
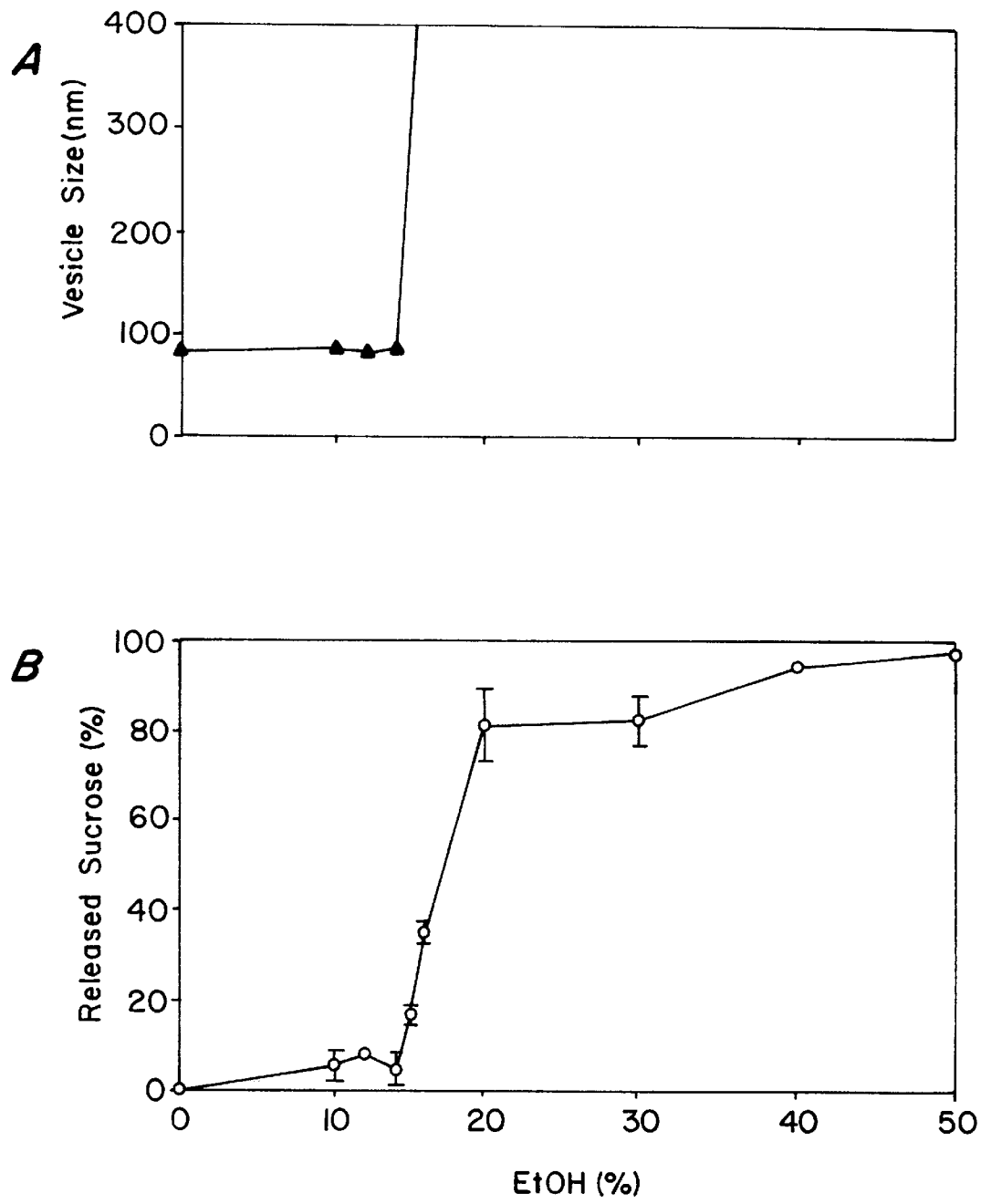
FIG. 5 shows the effect of ethanol on DPPC vesicles: (A) vesicle size and (B) permeability to sucrose.

DPPC vesicles, sized by extrusion through 100 nm pore size filters and containing [$^{14}$C]sucrose (1 mM), were incubated for 30 m at 25° C. in the buffer/ethanol mixtures indicated in FIG. 5. Aliquots were removed and the mean diameter determined by QELS analysis (FIG. 5A). The % release of sucrose (FIG. 5B) was measured following gel filtration as described in Methods.

Figure 6:
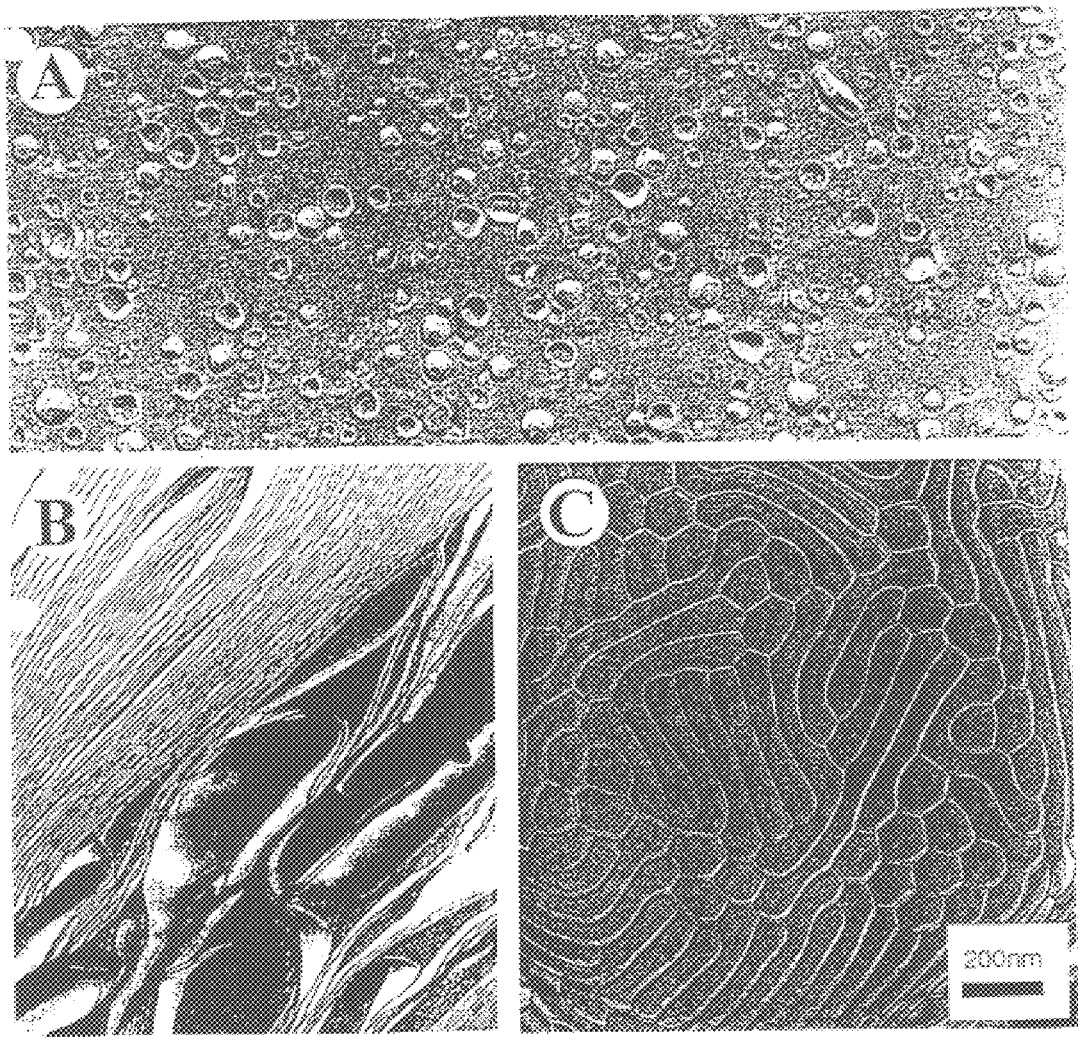
FIG. 6 shows freeze-fracture micrographs of DPPC vesicles (A) 0% ethanol and (B,C) 30% ethanol.

FIG. 5 shows the relationship between the ethanol induced increase in vesicle size and sucrose release for 100 nm vesicles of DPPC at 25° C. and therefore below the gel to liquid crystalline phase transition ($T_c$) of DPPC. There is a clear difference when compared to the EPC data shown in FIG. 2. The DPPC vesicles fuse into large structures at a much lower ethanol concentration at which point there is a rapid loss of sucrose. Consequently, for DPPC vesicles there is not a range of ethanol concentrations in which vesicle structure can be maintained with enhanced permeability properties. The abrupt collapse in structure and loss of sucrose is consistent with the formation of interdigitated sheets (P. L. Ahl et al. (1994) "Interdigitation-fusion: a new method for producing lipid vesicles of high internal volume" *Biochimica Et Biophysica Acta* 1195:237–244; L. T. Boni (1993) "Curvature dependent induction of the interdigitated gel phase in DPPC vesicles" *Biochimica Et Biophysica Acta* 1146:247–257) which were also observed by freeze-fracture and shown in FIG. 6. Panel A is a typical fracture plane obtained from vesicles composed of saturated lipid (100 nm DPPC vesicles before mixing with ethanol) in the absence of cholesterol and quenched from a temperature in which they are in the gel state (M. J. Hope et al. (1989) "Freeze-fracture of lipids and model membrane systems" [Review] *Journal of Electron Microscopy Technique* 13:277–287). The vesicles exhibit an angular outline which is commonly seen with saturated lipids. The angular appearance is thought to arise from the inability of phospholipid bilayers in a rigid gel state to bend smoothly around the acute curvature (R. Nayar et al. (1989) "Generation of large unilamellar vesicles from long chain saturated phosphatidylcholine" *Biochimica Et Biophysica Acta* 986:200–206). Panel B shows DPPC vesicles in 30% (v/v) ethanol. They show a fracture face characteristic of an interdigitated phase. In the presence of 30% ethanol, it is clear that vesicular structure has collapsed and fracture faces are observed which resemble tightly packed bilayers and ribbon like structures (panel B) which are commonly observed in lipid mixtures shown by other techniques to be interdigitated (L. T. Boni (1993) "Curvature dependent induction of the interdigitated gel phase in DPPC vesicles" *Biochimica Et Biophysica Acta* 1146:247–257). Occasionally, patterned structures are also seen (panel C) which are characteristic of saturated phospholipids viewed by freeze-fracture electron microscopy (M. J. Hope et al. (1989) "Freeze-fracture of lipids and model membrane systems" [Review] *Journal of Electron Microscopy Technique* 13:277–287). These results clearly demonstrate that the membrane permeability of vesicles composed of saturated lipids such as DPPC cannot be temporarily enhanced by ethanol as the alcohol destroys vesicle structure.

IV. Effect of Cholesterol on Ethanol Induced Permeability to sucrose

Figure 7:
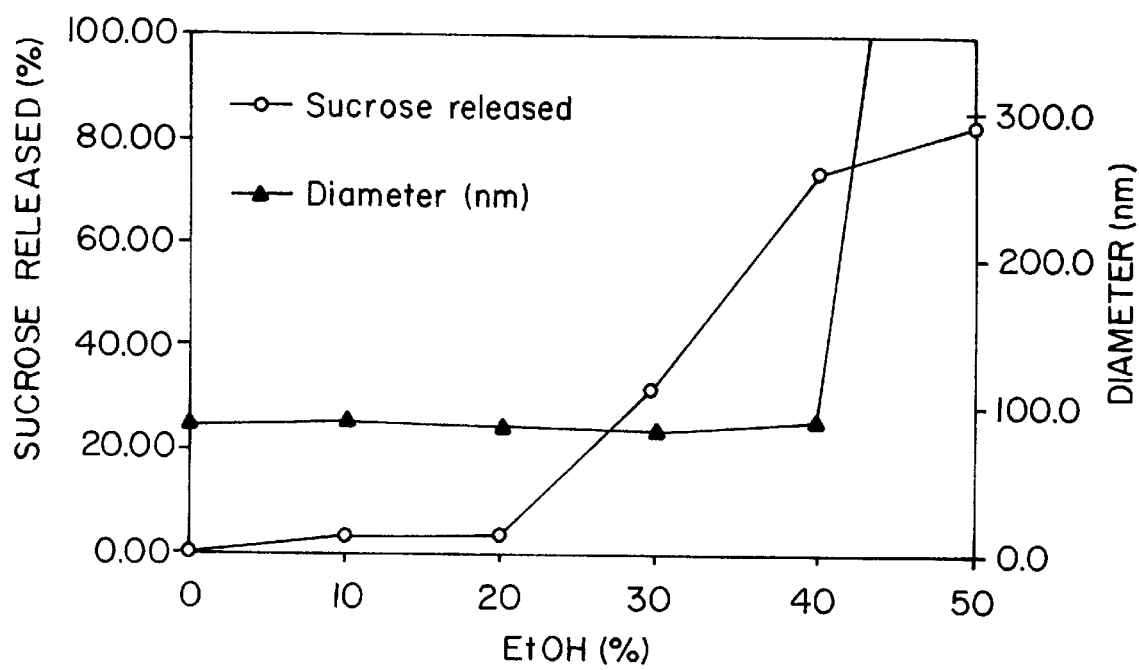
FIG. 7 shows the effect of ethanol on EPC/cholesterol vesicles: vesicle size and permeability to sucrose.

EPC/cholesterol (55:45 mol/mol) vesicles, sized by extrusion through 100 nm pore size filters and containing [$^{14}$C] sucrose (1 mM), were incubated for 30 m at 25° C. in the buffer/ethanol mixtures as indicated in FIG. 7. Aliquots were removed and the mean diameter determined by QELS analysis (FIG. 7A). The % release of sucrose (FIG. 7B) was measured following gel filtration as described in Methods. FIG. 7 shows that vesicles composed of EPC/cholesterol (55:45 mol/mol) retain their size (100 nm) over the same range of ethanol concentrations observed for EPC alone (FIG. 2). However, the permeability to sucrose is decreased such that during the 30 m incubation, approximately 30% of the encapsulated sucrose is released from vesicles containing cholesterol compared to 100% from EPC alone.

Figure 8:
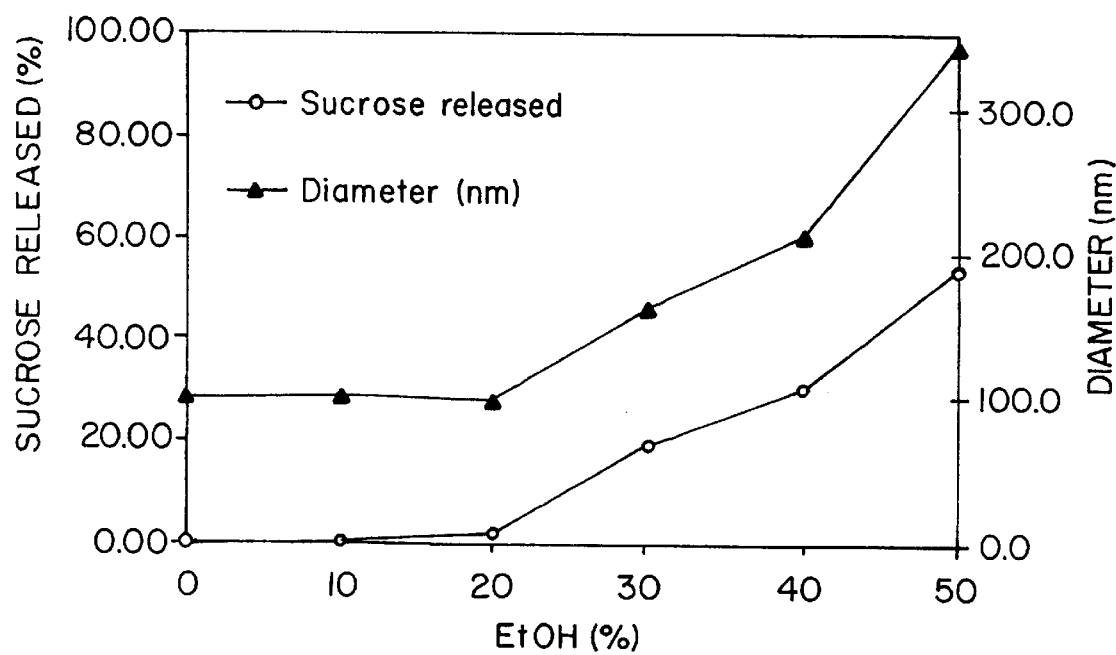
FIG. 8 shows the effect of ethanol on DPPC/cholesterol vesicles: vesicle size and permeability to sucrose.
Figure 9:
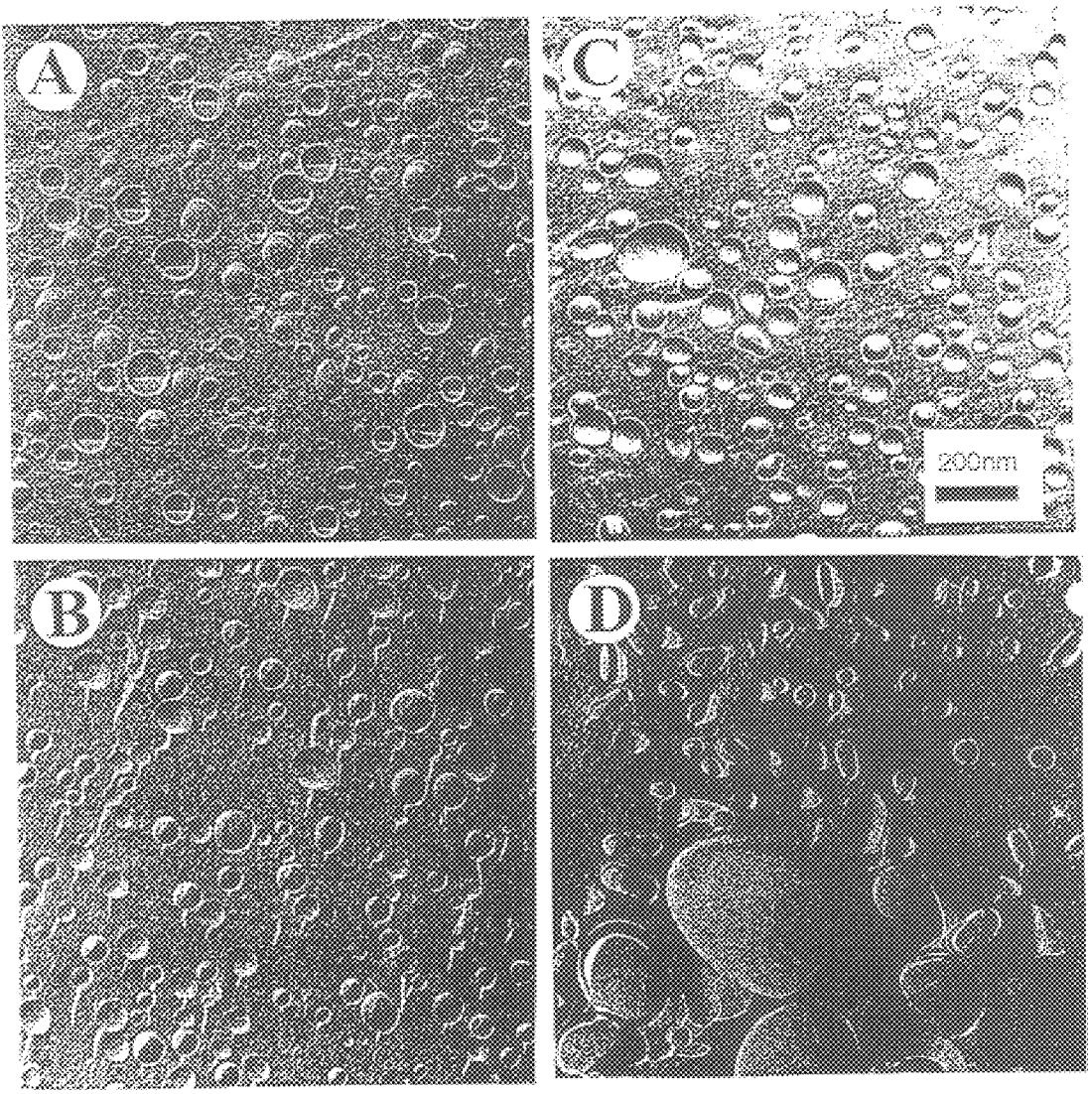
FIG. 9 shows freeze-fracture micrographs of EPC/cholesterol and DPPC/cholesterol vesicles before (upper panels A and C) and after (lower panels B and D) the addition of ethanol.

DPPC/cholesterol (55:45 mol/mol) vesicles, sized by extrusion through 100 nm pore size filters and containing [$^{14}$C]sucrose (1 mM), were incubated for 30 m at 25° C. in the buffer/ethanol mixtures as indicated in FIG. 8. Aliquots were removed and the mean diameter determined by QELS analysis. The % release of sucrose was measured following gel filtration as described in Methods. The effect of cholesterol on DPPC vesicles is presented in FIG. 8. In the absence of cholesterol, ethanol induces a collapse of vesicular structure at a concentration of 14% (v/v), as shown in FIG. 5. However, the presence of sterol prevents DPPC from entering the interdigitated phase (P. L. Ahl et al. (1994) "Interdigitation-fusion: a new method for producing lipid vesicles of high internal volume" *Biochimica Et Biophysica Acta* 1195:237–244; H. Komatsu et al. (1993) "Effect of unilamellar vesicle size on ethanol-induced interdigitation in dipalmitoylphosphatidylcholine," *Chemistry & Physics of Lipids* 65:11–21; J. W. Zeng and P. L. Chong (1991) "Interactions between pressure and ethanol on the formation of interdigitated DPPC liposomes: a study with Prodan fluorescence" *Biochemistry* 30:9485–9491; L. L. Herold (1987) "13C-NMR and spectrophotometric studies of alcohol-lipid interactions" *Chemistry & Physics of Lipids* 43:215–225), and so ethanol does not destroy vesicle structure (see micrographs in FIG. 9) but induces sufficient fusion to significantly increase the mean diameter of the population as measured by QELS. This is associated with some leakage of sucrose. FIG. 9A shows freeze-fracture micrographs of EPC/cholesterol vesicles (100 nm) before mixing with ethanol. FIG. 9B shows freeze-fracture micrographs of EPC/ cholesterol vesicles (100 nm) in the presence of 30% ethanol. These showed that the addition of ethanol to EPC/ cholesterol vesicles has no detectable effect on overall vesicle structure. This is supported by QELS data which did not detect any change in the mean diameter of 100 nm for the population.

FIG. 9C and FIG. 9D show freeze-fracture micrographs of DPPC/cholesterol vesicles before mixing with ethanol and in the presence of 30% ethanol respectively. DPPC/ cholesterol vesicles had clearly fused to form some large structures which are responsible for the increase in mean diameter of the population. QELS analysis showed that the mean diameter for DPPC/cholesterol vesicles incubated in 30% ethanol (the vesicle population in panel D of FIG. 9) increased to 180 nm.

V. Effect of Ethanol on Vesicle Permeability to Large Molecules

EPC vesicles, sized by extrusion through 100 nm pore size filters and containing either [$^{14}$C]sucrose (1 mM), [$^3$H]inulin or [$^3$H]dextran (both trace) were incubated at 25° C. in 30% ethanol. Aliquots were removed and the % release of contents was measured following gel filtration as described in Methods. The data are shown in FIG. 10.

Figure 10:
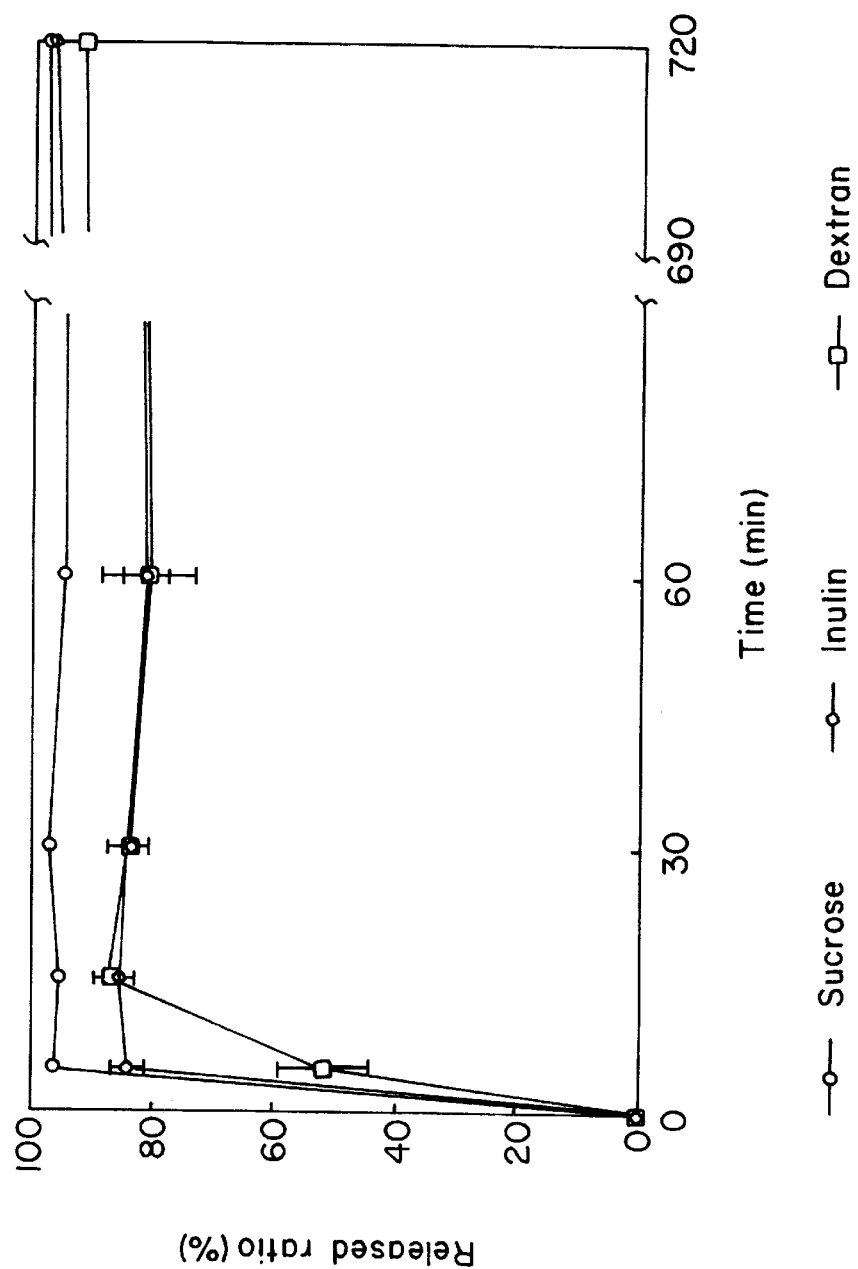
FIG. 10 shows the effect of ethanol on the release of sucrose, inulin and dextran from 100 nm EPC vesicles.

The data in FIG. 10 show that EPC vesicles loaded with either sucrose (Mwt~300), inulin (Mwt~5000) or dextran (Mwt~40,000) release their contents within 30 m in the presence of 30% ethanol. The diffusion of the higher molecular weight molecules out of vesicles is detectably slower than that of sucrose and this difference is more pronounced in the presence of cholesterol (data not shown). However, it is clear that ethanol is able to dramatically enhance the permeability of even dextran with a Mwt~40, 000.

Figure 11:
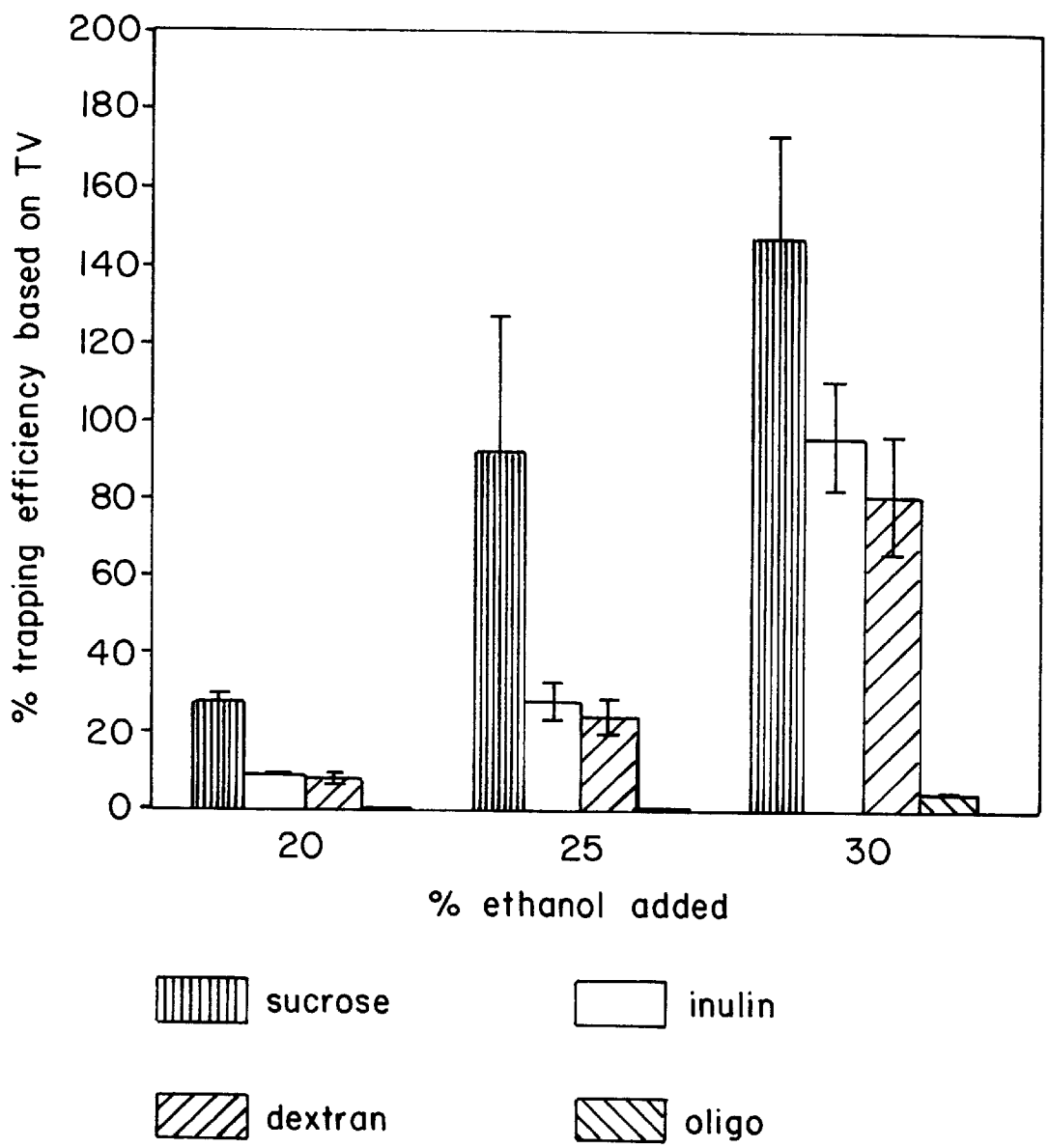
FIG. 11 shows the loading of various molecules into 100 nm EPC vesicles using ethanol to enhance membrane permeability.

FIG. 11 shows data on the ability of a highly charged, twenty base oligonucleotide to penetrate EPC vesicles. In this experiment, FITC-oligonucleotide, [$^{14}$C]sucrose [$^3$H] inulin and [$^3$H]dextran were incubated with 100 nm EPC vesicles (sized by extrusion through 100 nm pore size filters) in the presence of 20, 25 and 30% ethanol. After 15 m, aliquots were removed and assayed for encapsulated material following gel filtration as described in Methods. The y-axis of FIG. 11 indicates the amount entrapped as a % of what would be expected at equilibrium if the vesicle trapped volume (TV) was 1.5 L/mole. The non-polar molecules entered vesicles as expected; however; the negatively charged oligonucleotide did not. This result was confirmed by encapsulating oligonucleotide in vesicles and incubating these vesicles in 30% ethanol. DNA release could not be detected.

Effect of Ethanol on the Encapsulation of Protein in Vesicles

DOPC vesicles, sized by extrusion through 100 nm pore size filters were incubated with either lactase or horseradish peroxidase at 25° C. in 30% ethanol (v/v). After 30 m the incubation mixture was separated by gel filtration as described in Methods. Enzyme activity was measured in the absence and presence of TX100.

Figure 12:
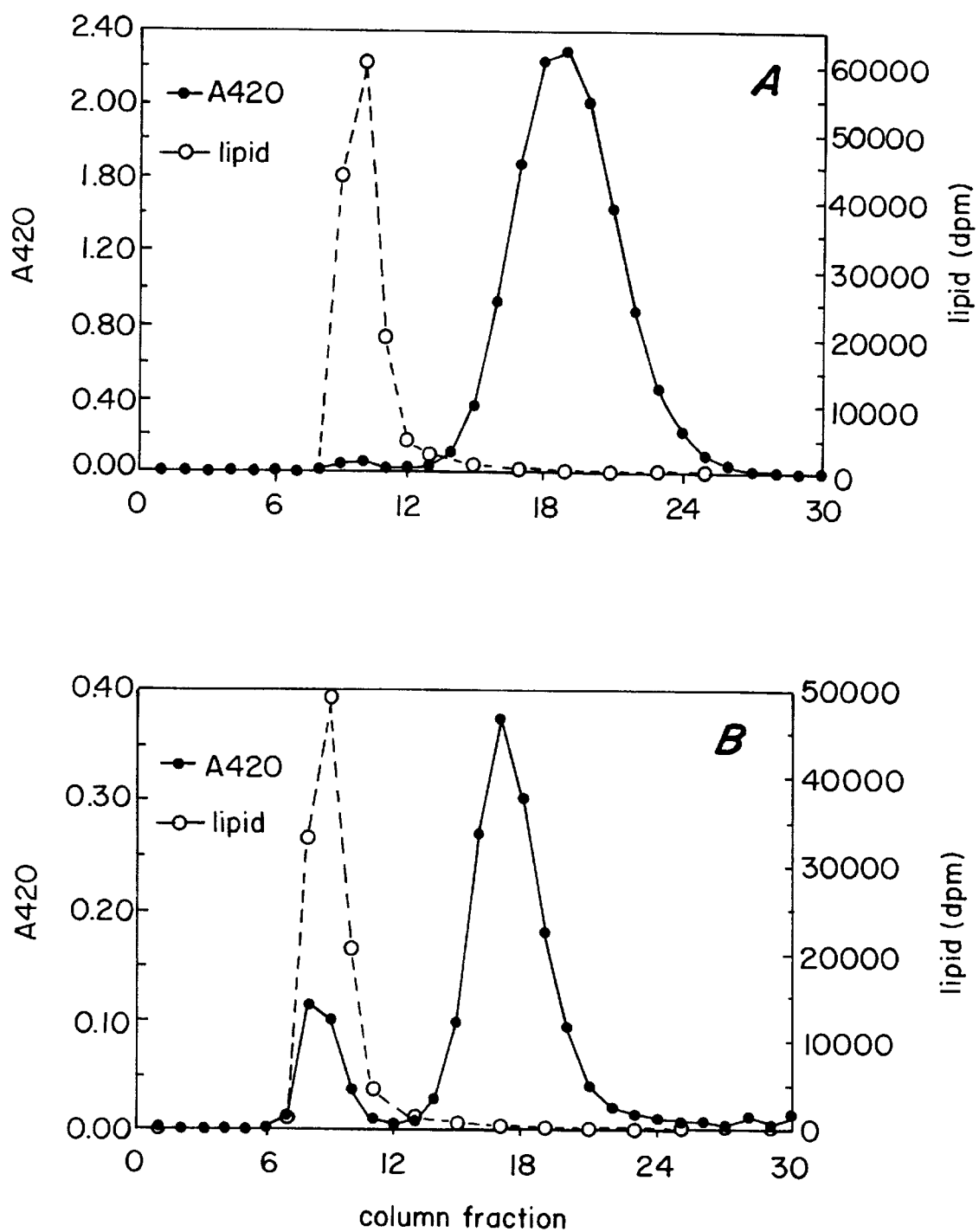
FIG. 12 shows the loading of lactase into preformed DOPC vesicles using ethanol.

Two enzymes were employed for this study, horseradish peroxidase (HRP) and lactase (or Lactozym™). Lactase (which was shown to be stable in the presence of 30% ethanol) was mixed with 100 nm EPC vesicles and ethanol was added to 30% (v/v). After 30 m the mixture was passed through a gel filtration column and each fraction assayed for lipid and enzyme activity in the presence and absence of the detergent TX100. The column profiles are shown in FIG. 12. FIG. 12A shows assays in the absence of TX100. FIG. 12B shows assays in the presence of TX100. They show that enzyme does become encapsulated after the ethanol treatment. Encapsulated activity can only be detected in the presence of detergent because the enzyme substrate is not able to penetrate the vesicle membrane; therefore, the vesicles containing protein display a latent enzyme activity.

HRP was also shown to penetrate the bilayer of DOPC and DOPC/cholesterol (1:1 mol/mol) vesicles in the presence of 30% ethanol. The enzyme and vesicles were incubated for 30 m at 46° C. and subsequently diluted 3-fold in phosphate buffered saline containing 0.2% bovine serum albumin. Untrapped HRP was removed by gel filtration and enzyme latency demonstrated using TX100 as above. This method has been used to prepare liposomes containing HRP for liposome binding assays.

What is claimed is:

1. A method of loading liposomes with a solute without causing vesicular collapse, said method comprising:

combining an aqueous solution having liposomes dispersed therein with the solute in a solution and an organic solvent which increases the membrane permeability of the liposomes to the solute, wherein the concentration of the organic solvent is at least about 10% v/v, whereby the solute enters the liposome by transmembrane permeation using a solute concentration gradient, and diluting the concentration of the organic solvent to an extent that decreases the membrane permeability of the liposome to the solute and trapping the solute in the liposome to provide a liposome loaded with solute.

2. The method of claim 1, wherein the organic solvent is added to a mixture of liposomes and solute in a solution.

3. The method of claim 1, wherein the organic solvent is an alcohol.

4. The method of claim 3, wherein the alcohol is selected from the group consisting of methyl alcohol, ethyl alcohol, n-propyl alcohol, isopropyl alcohol and n-butyl alcohol, sec-butyl alcohol and tert-butyl alcohol.

5. The method of claim 1, wherein the liposome comprises a phospholipid.

6. The method of claim 5, wherein the phospholipid is an unsaturated phospholipid.

7. The method of claim 6, wherein the phospholipid is egg phosphatidylcholine.

8. The method of claim 1, wherein the solute is a substantially uncharged species.

9. The method of claim 1, wherein the solute is a drug.

10. The method of claim 1, wherein the solute is a protein.

11. A method of changing the concentration of a solute in a liposome by increasing the membrane permeability of the liposome to the solute while maintaining the liposome at a substantially unaltered size, said method comprising:

providing a dispersion of liposomes and the solute, wherein the concentration of the solute in the liposome and outside the liposome are different, adding an organic solvent which increases the membrane permeability of the liposome to the solute, wherein the concentration of the organic solvent is at least about 10% v/v, whereby the solute enters or leaves the liposome by transmembrane permeation, provided the solute concentrations in and outside the liposome remain different, thereby changing the concentration of the solute in the liposome.

12. The method of claim 11, wherein the organic solvent is an alcohol.

13. The method of claim 12, wherein the alcohol is selected from the group consisting of methyl alcohol, ethyl alcohol, n-propyl alcohol, isopropyl alcohol and n-butyl alcohol, sec-butyl alcohol and tert-butyl alcohol.

14. The method of claim 11, wherein the liposome comprises a phospholipid.

15. The method of claim 14, wherein the phospholipid is an unsaturated phospholipid.

16. The method of claim 15, wherein the phospholipid is egg phosphatidylcholine.

17. The method of claim 11, wherein the solute is a substantially uncharged species.

18. The method of claim 11, wherein the solute is a drug.

19. The method of claim 11, wherein the solute is a protein.

20. A method of loading liposomes with a solute without causing vesicular collapse, said method comprising:

providing a dispersion of liposomes, solute and an organic solvent which increases the membrane permeability of the liposomes to the solute, wherein the concentration of the organic solvent is at least about 10% v/v and, wherein the concentration of solute in the liposome is less than the concentration of solute outside the liposome, incubating the dispersion for a time sufficient for the solute to enter the liposome by transmembrane permeation, and diluting the concentration of the organic solvent thereby decreasing the membrane permeability of the liposome to the solute and trapping the solute in the liposome to provide a liposome loaded with solute.

* * * * *